United States Patent
Murray et al.

(10) Patent No.: US 9,801,914 B2
(45) Date of Patent: *Oct. 31, 2017

(54) PREVOTELLA HISTICOLA PREPARATIONS AND THE TREATMENT OF AUTOIMMUNE CONDITIONS

(71) Applicant: Mayo Foundation for Medical Education and Research, Rochester, MN (US)

(72) Inventors: Joseph A. Murray, Rochester, MN (US); Eric V. Marietta, Rochester, MN (US); Susan H. Barton, Reston, VA (US); Veena Taneja, Rochester, MN (US); Ashutosh Mangalam, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/385,554

(22) Filed: Dec. 20, 2016

(65) Prior Publication Data

US 2017/0189455 A1 Jul. 6, 2017

Related U.S. Application Data

(63) Continuation of application No. 14/643,156, filed on Mar. 10, 2015, now Pat. No. 9,555,066, which is a continuation of application No. 14/086,090, filed on Nov. 21, 2013, now Pat. No. 9,005,603, which is a continuation of application No. 13/505,169, filed as application No. PCT/US2010/054314 on Oct. 27, 2010, now Pat. No. 8,617,536.

(60) Provisional application No. 61/299,068, filed on Jan. 28, 2010, provisional application No. 61/256,731, filed on Oct. 30, 2009.

(51) Int. Cl.
| | |
|---|---|
| *A61K 35/741* | (2015.01) |
| *A61K 35/74* | (2015.01) |
| *A61K 9/00* | (2006.01) |
| *A23L 33/135* | (2016.01) |
| *C12R 1/01* | (2006.01) |

(52) U.S. Cl.
CPC .......... *A61K 35/74* (2013.01); *A61K 9/0053* (2013.01); *A23L 33/135* (2016.08); *A61K 9/00* (2013.01); *A61K 35/741* (2013.01); *C12R 1/01* (2013.01)

(58) Field of Classification Search
None
See application file for complete search history.

(56) References Cited

U.S. PATENT DOCUMENTS

| | | | |
|---|---|---|---|
| 8,617,536 B2 | 12/2013 | Murray et al. | |
| 9,005,603 B2 | 4/2015 | Murray et al. | |
| 9,555,066 B2 | 1/2017 | Murray et al. | |
| 2004/0170617 A1 | 9/2004 | Finegold | |
| 2007/0154414 A1 | 7/2007 | Bonfiglio | |
| 2008/0241226 A1 | 10/2008 | Abeln et al. | |
| 2014/0105972 A1 | 4/2014 | Murray et al. | |
| 2015/0290256 A1 | 10/2015 | Murray et al. | |

OTHER PUBLICATIONS

Alauzet et al., "*Prevotella nanceiensis* sp. nov., isolated from human clinical samples," *International J Systematic Evol. Microbiol.*, 2007, 27:2216-2220.

Bradley et al., "HLA-DQB1 polymorphism determines incidence, onset, and severity of collagen-induced arthritis in transgenic mice. Implications in human rheumatoid arthritis," *J Clin. Invest.*, 1997, 100:2227-2234.

Brehm et al., Cold Spring Harb. Perpect. Med. 2(5):1-13, May 2012.

Das et al., "Complementation between specific HLA-DR and HLA-DQ genes in transgenic mice determines susceptibility to experimental autoimmune encephalomyelitis," *Hum. Immunol.*, 2000, 61:279-289.

Downes et al., "*Prevotella histicola* sp. nov., isolated for the human oral cavity," *International J. Systematic Evol. Microbiol.*, 2008, 58:1788-1791.

GenBank Accession No. EF405529.1, GI: 126143367, "*Prevotella nanceiensis* strain LBN 297 16S ribosomal RNA gene, partial sequence," Oct. 4, 2007, 1 page.

GenBank Accession No. EU126662.1, GI: 157366663, "*Prevotella histicola* strain N12-20 16S ribosomal RNA gene, partial sequence," Sep. 9, 2008, 1 page.

GenBank Accession No. NP 000524, GI: 41349499, "myelin proteolipid protein isoform 1 [*Homo sapiens*]," Feb. 17, 1991, 3 pages.

Griffiths et al., "Immunogenetic control of experimental type II collagen-induced arthritis. I. Susceptibility and resistance among inbred strains of rats," *Arthritis Rheum.*, 1981, 24:781-789.

International Preliminary Report on Patentability in International Application No. PCT/US2010/054314, mailed May 10, 2012, 8 pages.

International Search Report and Written Opinion in International Application No. PCT/US2010/054314, mailed Jul. 22, 2011, 13 pages.

Jackson et al., "The effect of the commensal bacterium, *Prevotella nanceiensis*, on experimental autoimmune encephalomyelitis, an animal model for multiple sclerosis," *Kentucky Acad. of Sci. Annual Meeting*, 2008, 30 pages.

Kaur et al., "Probiotics: delineation of prophylactic and therapeutic benefits," *J Medicinal Food*, 2009, 12(2):219-235.

Lampson et al., "Two populations of Ia-like molecules on a human B cell line," *J. Immunol.*, 1980, 125:293-299.

(Continued)

*Primary Examiner* — S. Devi
(74) *Attorney, Agent, or Firm* — Fish & Richardson P.C.

(57) ABSTRACT

This document provides methods and materials related to *Prevotella histicola* preparations. For example, *Prevotella histicola* preparations in the form of an oral medicament or dietary supplement (e.g., a pill, tablet, capsule) are provided. In addition, methods and materials for using a *Prevotella histicola* preparation provided herein as an anti-inflammatory agent are provided.

7 Claims, 15 Drawing Sheets

(56) References Cited

OTHER PUBLICATIONS

Mangalam et al., "HLA-DQ8 (DQB1*0302)-Restricted Th17 Cells Exacerbate Experimental Autoimmune Encephalomyelitis in HLA-DR3-Transgenic Mice," *J. Immunol.*, 2009, 182(8):5131-5139.
Marques et al., "Septic arthritis of the knee due to *Prevotella loescheii* following tooth extraction," *Med. Oral Pathol. Oral Cir. Bucal.*, 2008, 13(8):E505-E507.
Mielcarz et al., "FTY720 Ameliorates Pathogen Driven Ileitis in C57BL/6 Mice by Impeding Lymphocyte Trafficking," *Clin Immunol.*, Jan. 2008, 127:S122.
Sampedro et al., "Species of *Propionibacterium* and *Propionibacterium acnes* phylotypes associated with orthopedic implants," *Diagnostic Microbiol Infect. Dis.*, 2009, 64:138-145.
Strauss et al., "Negative and positive selection by HLA-DR3(DRw17) molecules in transgenic mice," *Immunogenetics*, 1994, 40:104-108.
Taneja et al., "Delineating the Role of the HLA-DR4 "Shared Epitope" in Susceptibility versus Resistance to Develop Arthritis," *J Immunol.*, 2008, 181:2869-2877.
Taneja et al., "New Humanized HLA-DR4-Transgenic Mice That Mimic the Sex Bias of Rheumatoid Arthritis," *Arthritis Rheum.*, 2007, 56:69-78.
Vaahtovuo et al., "Fecal Microbiota in Early Rheumatoid Arthritis," *J Rheumatol.*, 2008, 35(8):1500-15005.
Wooley, "Type II collagen-induced arthritis in mice. I. Major histocompatibility complex (I region) linkage and antibody correlates," *J Exp. Med.*, 1981, 154:688-700.

Figure 5
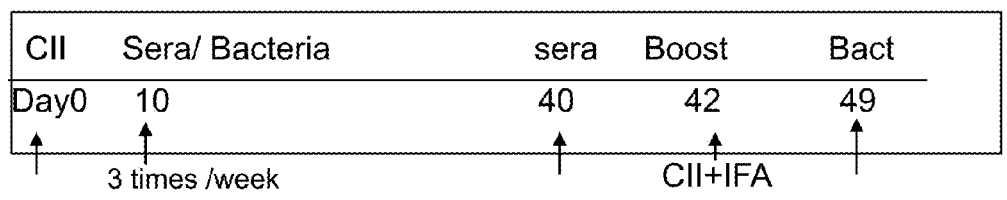
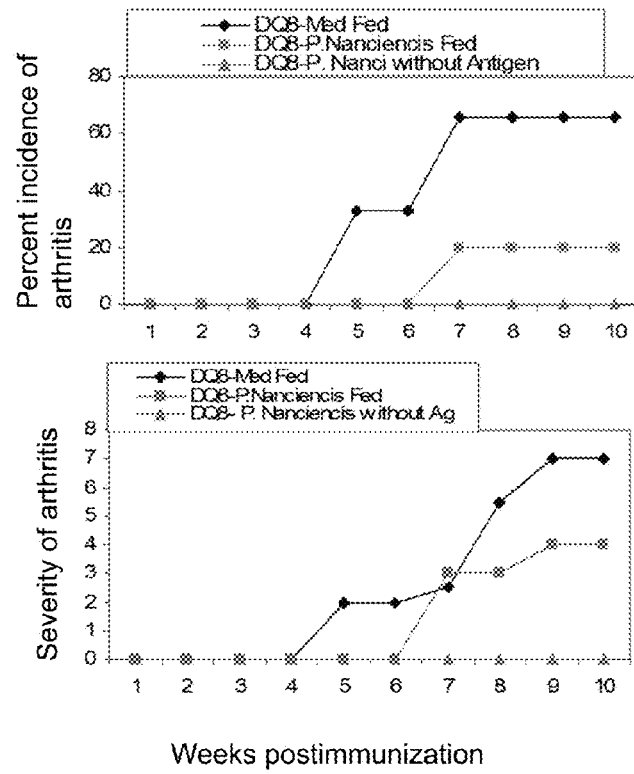
Weeks postimmunization

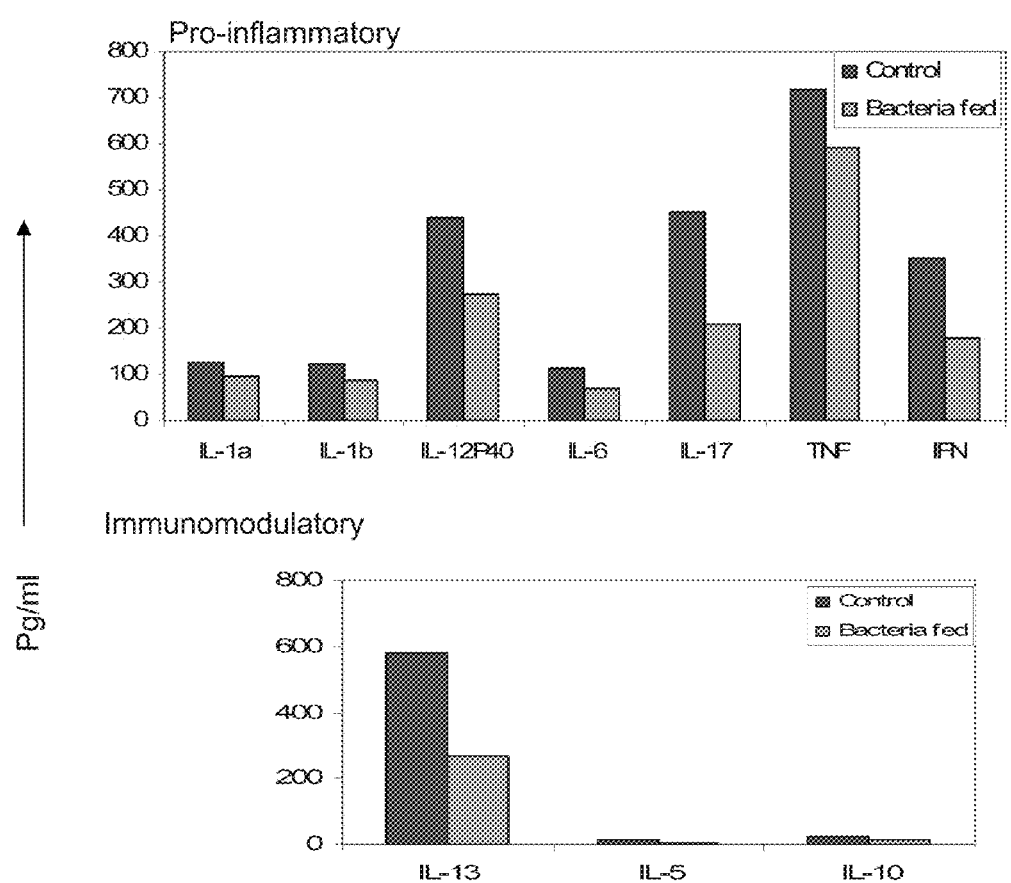

Figure 10

EU126662.1 Prevotella histicola strain N12-20 16S ribosomal RNA gene, partial sequence
Length=1453

Score = 850 bits (460), Expect = 0.0
Identities = 464/466 (99%), Gaps = 1/466 (0%)
Strand=Plus/Plus

```
Query  1    GGCTT-ACACATGCAAGTCGAGGGGAAACGGCATTAAGTGCTTGCACTTTTTGGACGTCG  59
            ||||| ||||||||||||||||||||||||||||||||||||||||||| |||||||||
Sbjct  18   GGCTTAACACATGCAAGTCGAGGGGAAACGGCATTAAGTGCTTGCACTTTTTGGACGTCG  77

Query  60   ACCGGCGCACGGGTGAGTAACGCGTATCCAACCTTCCCATGACTAAGGGATAACCTGCCG  119
            ||||||||||||||||||||||||||||||||||||||||||||||||||||||||||||
Sbjct  78   ACCGGCGCACGGGTGAGTAACGCGTATCCAACCTTCCCATGACTAAGGGATAACCTGCCG  137

Query  120  AAAGGCAGACTAATACCTTATGGTCTTCACTGACGGCATCAGATGTGAAGTAAAGATTTA  179
            ||||||||||||||||||||||||||||||||||||||||||||||||||||||||||||
Sbjct  138  AAAGGCAGACTAATACCTTATGGTCTTCACTGACGGCATCAGATGTGAAGTAAAGATTTA  197

Query  180  TCGGTTATGGATGGGGATGCGTCTGATTAGCTTGTTGGCGGGGTAACGGCCCACCAAGGC  239
            ||||||||||||||||||||||||||||||||||||||||||||||||||||||||||||
Sbjct  198  TCGGTTATGGATGGGGATGCGTCTGATTAGCTTGTTGGCGGGGTAACGGCCCACCAAGGC  257

Query  240  AACGATCAGTAGGGGTTCTGAGAGGAAGGTCCCCCACATTGGAACTGAGACACGGTCCAA  299
            ||||||||||||||||||||||||||||||||||||||||||||||||||||||||||||
Sbjct  258  AACGATCAGTAGGGGTTCTGAGAGGAAGGTCCCCCACATTGGAACTGAGACACGGTCCAA  317

Query  300  ACTCCTACGGGAGGCAGCAGTGAGGAATATTGGTCAATGGGCGAGAGCCTGAACCAGCCA  359
            ||||||||||||||||||||||||||||||||||||||||||||||||||||||||||||
Sbjct  318  ACTCCTACGGGAGGCAGCAGTGAGGAATATTGGTCAATGGGCGAGAGCCTGAACCAGCCA  377

Query  360  AGTAGCGTGCAGGATGACGGCCCTATGGGTTGTAAACTGCTTTTGTATGGGGATAAAGTC  419
            ||||||||||||||||||||||||||||||||||||||||||||||||||||||||||||
Sbjct  378  AGTAGCGTGCAGGATGACGGCCCTATGGGTTGTAAACTGCTTTTGTATGGGGATAAAGTC  437

Query  420  ANTCACGTGTGATTGTTTGCAGGTACCATACGAATAAGGACCGGCT  465
            | ||||||||||||||||||||||||||||||||||||||||||||
Sbjct  438  AGTCACGTGTGATTGTTTGCAGGTACCATACGAATAAGGACCGGCT  483
```

US 9,801,914 B2

PREVOTELLA HISTICOLA PREPARATIONS AND THE TREATMENT OF AUTOIMMUNE CONDITIONS

CROSS-REFERENCE TO RELATED APPLICATIONS

This application is a continuation of U.S. application Ser. No. 14/643,156, filed Mar. 10, 2015 (now U.S. Pat. No. 9,555,066), which is a continuation of U.S. application Ser. No. 14/086,090, filed Nov. 21, 2013 (now U.S. Pat. No. 9,005,603), which is a continuation of U.S. application Ser. No. 13/505,169 (now U.S. Pat. No. 8,617,536), filed Apr. 30, 2012, which is a National Stage application under 35 U.S.C. §371 and claims benefit under 35 U.S.C. §119(a) of International Application No. PCT/US2010/054314, having an International Filing Date of Oct. 27, 2010, which claims the benefit of priority to U.S. Provisional Application Ser. No. 61/299,068, filed on Jan. 28, 2010 and U.S. Provisional Application Ser. No. 61/256,731, filed on Oct. 30, 2009. The disclosures of the prior applications are considered part of (and are incorporated by reference in) the disclosure of this application.

STATEMENT AS TO FEDERALLY SPONSORED RESEARCH

This invention was made with government support under DK071003 awarded by the National Institutes of Health. The government has certain rights in the invention.

BACKGROUND

1. Technical Field

This document relates to *Prevotella histicola* preparations and the use of *Prevotella histicola* preparations to treat autoimmune conditions (e.g., arthritis and multiple sclerosis).

2. Background Information

A large reservoir of microorganisms lives in the digestive tracts of animals and is often referred to as the gut flora or microflora. Bacteria make up most of the flora in the colon and about 60 percent of the dry mass of feces. In fact, between 300 and 1000 different species may live in the gut.

SUMMARY

This document provides methods and materials related to *Prevotella histicola* preparations. For example, this document provides *Prevotella histicola* preparations in the form of an oral medicament or dietary supplement (e.g., a pill, tablet, capsule). In addition, this document provides methods for using a *Prevotella histicola* preparation provided herein as an anti-inflammatory agent. In some cases, a *Prevotella histicola* preparation provided herein can be used as an oral anti-inflammatory medicament or dietary supplement to treat autoimmune conditions such as arthritis and multiple sclerosis. The *Prevotella histicola* preparations provided herein can contain live or killed *Prevotella histicola* microorganisms. In some cases, a composition including, or consisting essentially of, a culture supernatant from a *Prevotella histicola* culture can be used as described herein. For example, a culture supernatant from a *Prevotella histicola* culture can be administered (e.g., orally administered) to a mammal to treat an autoimmune condition or inflammatory condition in the mammal. Such a culture supernatant can include live or killed *Prevotella histicola* microorganisms. In some cases, a culture supernatant from a *Prevotella histicola* culture can lack live *Prevotella histicola* microorganisms. In some cases, a culture supernatant from a *Prevotella histicola* culture can include lysed *Prevotella histicola* microorganisms. Any appropriate media can be used to culture *Prevotella histicola* microorganisms to form a culture supernatant. For example, broth (e.g., trypticase soy broth) can be used to culture *Prevotella histicola* microorganisms to form a culture supernatant.

The *Prevotella histicola* preparations and compositions provided herein and the methods for using the *Prevotella histicola* preparations and compositions provided herein can allow medical professionals to treat mammals (e.g., human patients) suffering from an autoimmune condition. In some cases, the methods and materials provided herein can allow humans to supplement their diets with bacterial organisms having the ability to reduce the severity or development of an autoimmune condition.

In general, one aspect of this document features a method for treating an autoimmune condition in a mammal. The method comprises, or consists essentially of, administering a composition comprising, or consisting essentially of, live *Prevotella histicola* to the mammal under conditions wherein the severity of the autoimmune condition is reduced. The mammal can be a human. The autoimmune condition can be multiple sclerosis. The autoimmune condition can be arthritis. The administering step can comprise an oral administration. The composition can be a pill, tablet, or capsule. The composition can be a pill, tablet, or capsule configured to deliver the live *Prevotella histicola* to the intestines of the mammal. The severity of the autoimmune condition can be reduced by greater than about 25 percent following the administering step. The severity of the autoimmune condition can be reduced by greater than about 50 percent following the administering step. The severity of the autoimmune condition can be reduced by greater than about 75 percent following the administering step. The method can comprise identifying the mammal as having the autoimmune condition prior to the administration. Representative cells of the *Prevotella histicola* can be the cells deposited as NRRL accession number B-50329.

In another aspect, this document features a nutritional supplement comprising, or consisting essentially of, live *Prevotella histicola*. The *Prevotella histicola* can be encapsulated to be released in the intestine of a mammal. Representative cells of the *Prevotella histicola* can be the cells deposited as NRRL accession number B-50329.

In another aspect, this document features a human food product supplemented with live *Prevotella histicola*. The product can contain between $1 \times 10^7$ to $1 \times 10^{11}$ cells of the *Prevotella histicola*. The product can be selected from the group consisting of milk, yogurt, milk powder, tea, juice, cookies, wafers, crackers, and cereals.

In another aspect, this document features a method for treating an autoimmune condition in a mammal. The method comprises, or consists essentially of, administering a composition comprising, or consisting essentially of, dead *Prevotella histicola* to the mammal under conditions wherein the severity of the autoimmune condition is reduced. The mammal can be a human. The autoimmune condition can be multiple sclerosis. The autoimmune condition can be arthritis. The administering step can comprise an oral administration. The composition can be a pill, tablet, or capsule. The composition can be a pill, tablet, or capsule configured to deliver the dead *Prevotella histicola* to the intestines of the mammal. The severity of the autoimmune condition can be reduced by greater than about 25 percent following the administering step. The severity of the autoimmune condition can be reduced by greater than about 50 percent following the administering step. The severity of the autoimmune condition can be reduced by greater than about 75 percent following the administering step. The method can comprise identifying the mammal as having the autoimmune condition prior to the administration. Representative cells of the *Prevotella histicola* can be the cells deposited as NRRL accession number B-50329.

In another aspect, this document features a nutritional supplement comprising, or consisting essentially of, dead *Prevotella histicola*. The *Prevotella histicola* can be encapsulated to be released in the intestine of a mammal. Representative cells of the *Prevotella histicola* can be the cells deposited as NRRL accession number B-50329.

In another aspect, this document features a human food product supplemented with dead *Prevotella histicola*. The product can contain between $1 \times 10^7$ to $1 \times 10^{11}$ cells of the *Prevotella histicola*. The product can be selected from the group consisting of milk, yogurt, milk powder, tea, juice, cookies, wafers, crackers, and cereals.

In another aspect, this document features a method for treating an autoimmune condition in a mammal. The method comprises, or consists essentially of, administering a composition comprising, or consisting essentially of, a culture supernatant from a *Prevotella histicola* culture to the mammal under conditions wherein the severity of the autoimmune condition is reduced. The mammal can be a human. The autoimmune condition can be multiple sclerosis. The autoimmune condition can be arthritis. The administering step can comprise an oral administration. The composition can be a pill, tablet, or capsule. The composition can be a pill, tablet, or capsule configured to deliver the culture supernatant to the intestines of the mammal. The severity of the autoimmune condition can be reduced by greater than about 25 percent following the administering step. The severity of the autoimmune condition can be reduced by greater than about 50 percent following the administering step. The severity of the autoimmune condition can be reduced by greater than about 75 percent following the administering step. The method can comprise identifying the mammal as having the autoimmune condition prior to the administration. Representative cells of the *Prevotella histicola* can be the cells deposited as NRRL accession number B-50329.

In another aspect, this document features a nutritional supplement comprising, or consisting essentially of, a culture supernatant from a *Prevotella histicola* culture. The culture supernatant can be encapsulated to be released in the intestine of a mammal. Representative cells of the *Prevotella histicola* can be the cells deposited as NRRL accession number B-50329.

In another aspect, this document features a human food product supplemented with a culture supernatant from a *Prevotella histicola* culture. The culture supernatant can be obtained from a culture having greater than $1 \times 10^3$ (e.g., greater than $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$) *Prevotella histicola* cells per mL of media. The product can be selected from the group consisting of milk, yogurt, milk powder, tea, juice, cookies, wafers, crackers, and cereals.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 4A *P. histicola* treated DR3DQ8 mice exhibited reduced levels of MIP-1α, MIP-1β, and MCP-1 in splenocytes as compared to levels measured in splenocytes from sham treated mice. FIG. 4B Levels of these chemokines were higher in splenocytes from *P. histicola* treated mice as compared to levels measured in splenocytes from sham treated mice.

FIG. 5. Modulation of collagen-induced arthritis (CIA) by *Prevotella histicola*. Immunization of HLA-DQ8.AEo Tg mice with type II collagen (CII) leads to development of collagen-induced arthritis, a model for rheumatoid arthritis (Taneja et al., *J. Immunol.*, 56:69-78 (2007)). Treatment with *P. histicola* protected DQ8.AEo mice from developing arthritis. Three groups of mice were included: (1) mice immunized with CII/CFA and treated with medium, (2) mice immunized with CII and treated with *P. histicola*, and (3) a control group, which included mice immunized with *P. histicola* without CII. Ten days post immunization, mice were gavaged three times per week with *P. histicola* ($2 \times 10^9$ CFU in 100 µL of TSB culture media) for up to 7 weeks. Group 1 and group 2 mice were boosted with CII/IFA in the $6^{th}$ week. Mice were monitored for arthritis for up to 10 weeks. Mice immunized with CII and treated with *P. histi-*

*cola* exhibited a dramatic decrease in disease incidence as well as milder disease. Mice only given *P. histicola* did not develop any arthritis.

Figure 6A:
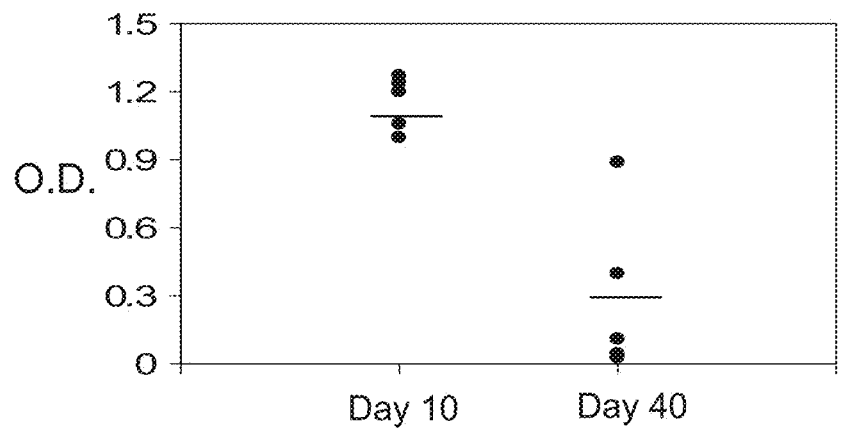
Figure 6B:
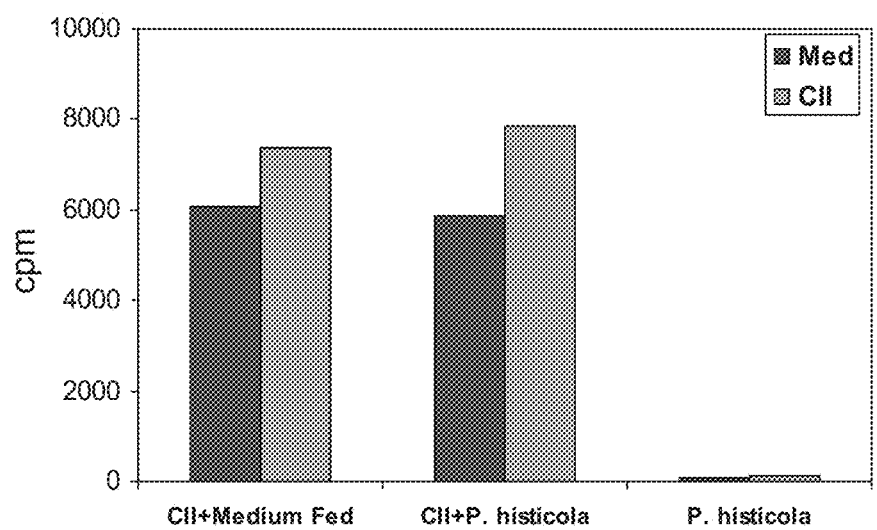

FIGS. 6A-B. *P. histicola* treated mice exhibited reduced humoral antigen-specific response. FIG. 6A Anti-CII antibodies in sera collected before and after treatment with *P. histicola* exhibited a reduction in antibodies. Anti-CII antibodies were tested by ELISA. FIG. 6B T cell proliferation to CII in vitro did not exhibit any significant reduction in *P. histicola* treated mice. Only *P. histicola* gavaged mice did not exhibit any antigen-specific response.

FIG. 7. All tested proinflammatory and immunomodulatory cytokines produced in response to CII were reduced in *P. histicola* treated mice compared to medium fed (control) mice. Cytokines were measured from serum of mice by using a multiplex array system.

Figure 8:
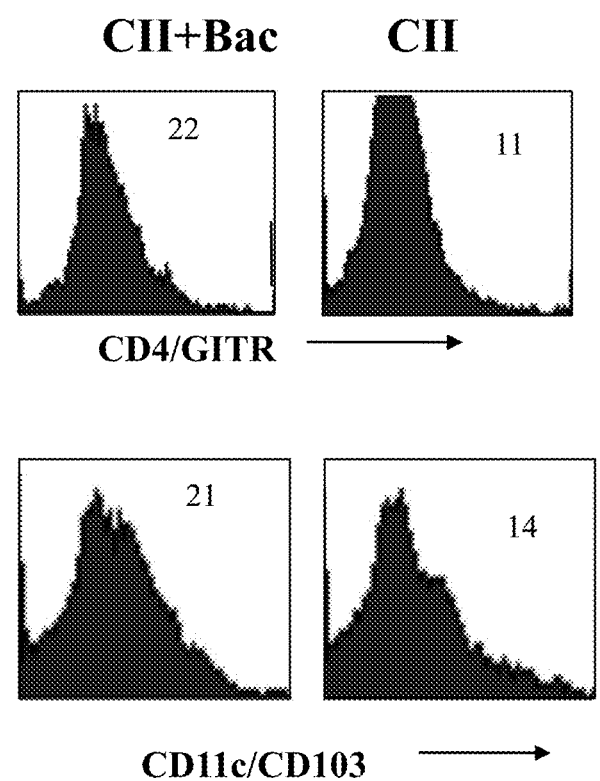

FIG. 8. Mice treated with *P. histicola* exhibited higher numbers of CD4$^+$GITR$^+$ T regulatory cells and CD11c$^+$ CD103$^+$ dendritic cells in splenocytes. The FACs analysis after staining with conjugated antibodies is shown.

Figure 9:
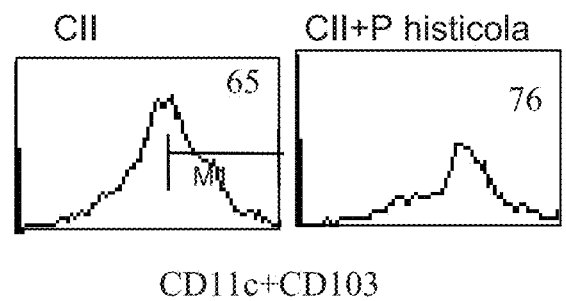

FIG. 9. Treatment with *P. histicola* leads to an increase in regulatory dendritic cells, CD11c$^+$CD103$^+$, in lamina propria.

FIG. 10 is a sequence comparison of 16S rRNA nucleic acid from *P. histicola* deposited with the ARS Culture Collection (NRRL accession number B 50329, deposited Oct. 28, 2009) and set forth as Query (SEQ ID NO:1) to 16S rRNA nucleic acid from GenBank® accession number EU126662.1 *Prevotella histicola* strain N12-20 (GI No.: 157366663) set forth as subject (Sbjct; SEQ ID NO:2).

Figure 11:
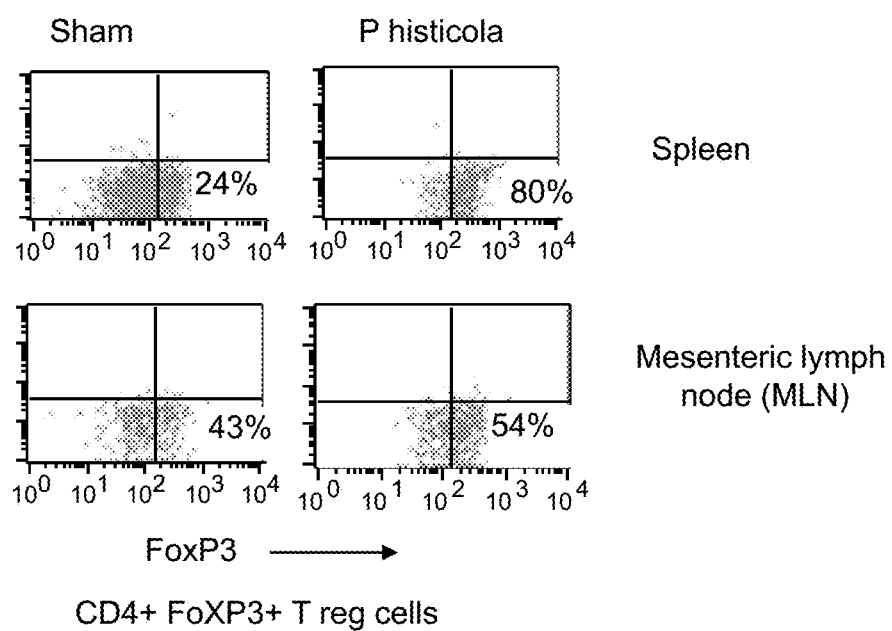

FIG. 11 contains flow cytometry graphs plotting the percentage of CD4$^+$FoxP3$^+$ cells in spleen or mesenteric lymph nodes from sham treated mice or *P. histicola* treated mice.

Figure 12:
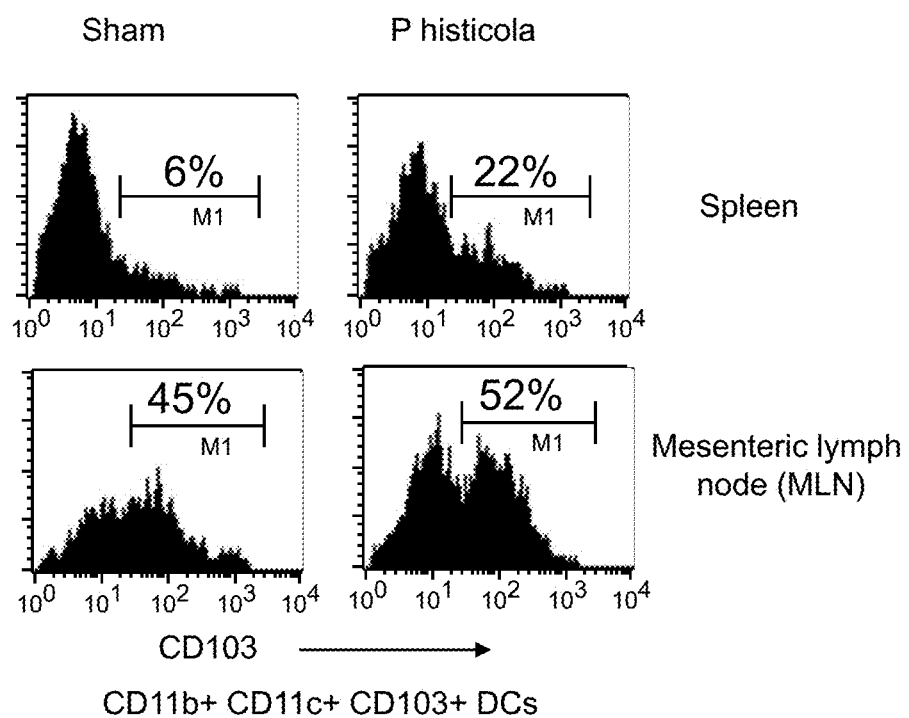

FIG. 12 contains flow cytometry histograms plotting the percentage of CD11b$^+$ CD11c$^+$ CD103$^+$ dendritic cells (DCs) in spleen or mesenteric lymph nodes from sham treated mice or *P. histicola* treated mice.

Figure 13A:
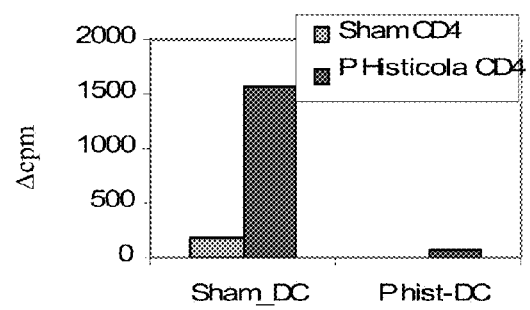
Figure 13B:
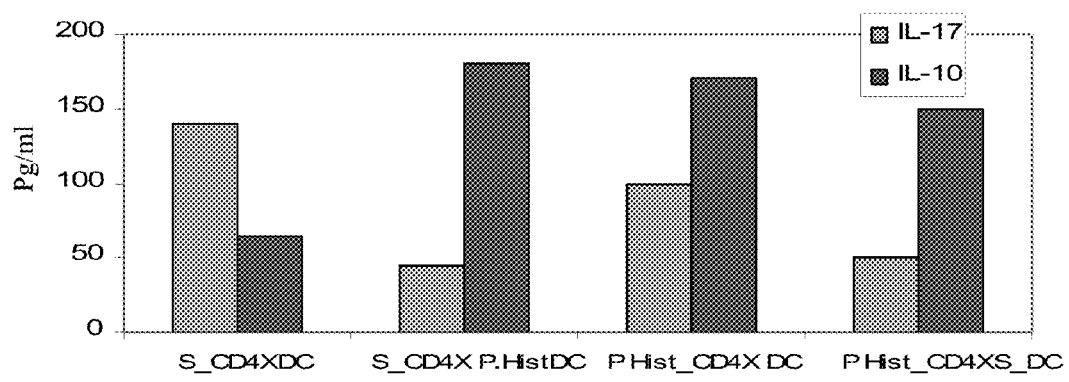

FIG. 13A is a graph plotting the level of proliferation (Δ cpm) for DCs isolated from sham treated or *P. histicola* treated mice and cultured with CD4$^+$ cells isolated from sham treated or *P. histicola* treated mice in the presence of CII. FIG. 13B is a graph plotting the levels of IL-10 and IL-17 (pg/nL) from CII containing cultures of either DCs isolated from sham treated or *P. histicola* treated mice in combination with either CD4$^+$ cells isolated from sham treated or *P. histicola* treated mice. The ratio of DCs to CD4$^+$ cells was 1:1. S represents sham treated, and P. hist. represents *P. histicola* treated.

Figure 14:
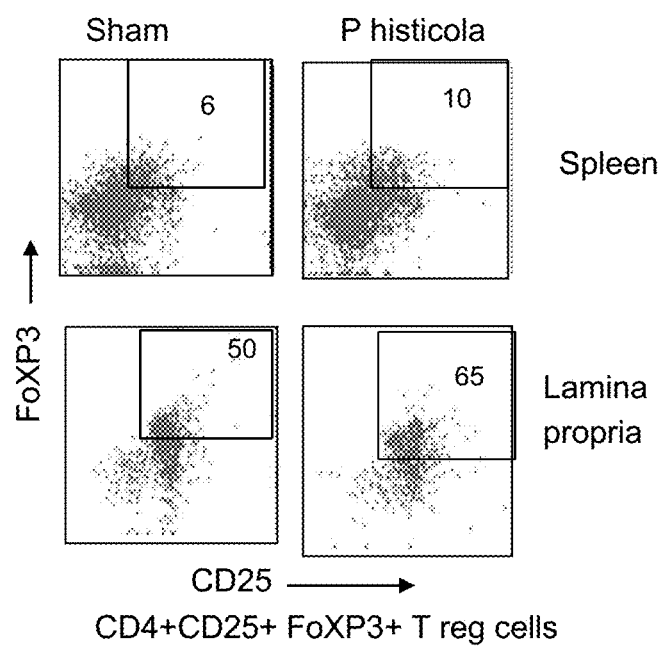

FIG. 14 contains flow cytometry graphs plotting the percentage of CD4$^+$CD25$^+$FoxP3$^+$ cells in spleen or lamina propria from sham treated mice or *P. histicola* treated mice.

Figure 15:
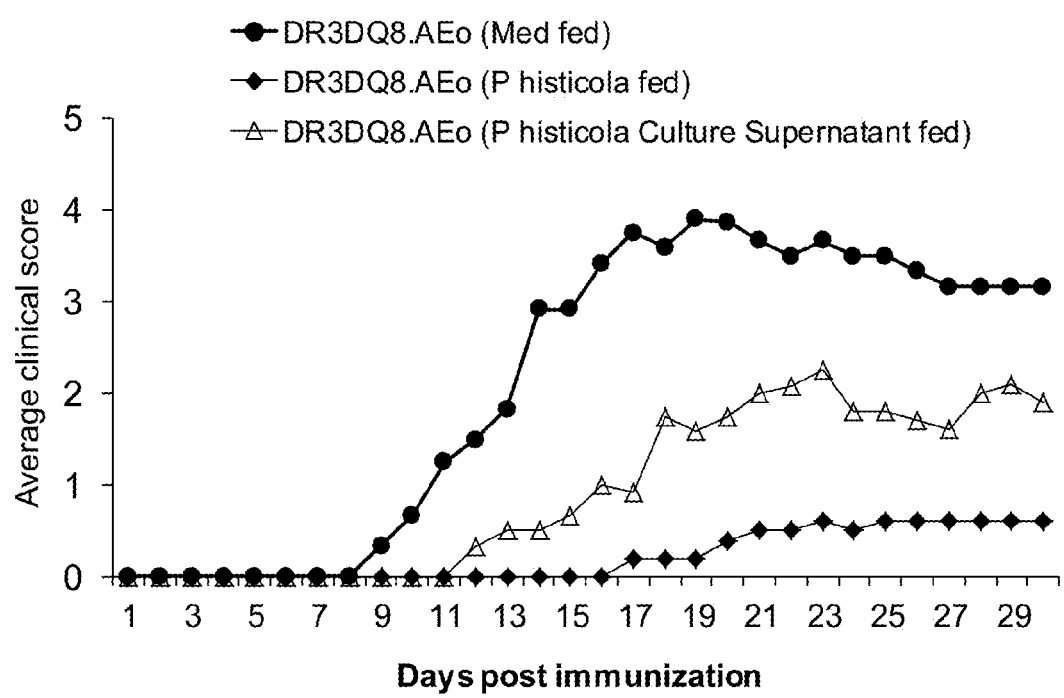

FIG. 15 is a graph plotting the average clinical score of EAE for mice treated with media allow (Med fed), *P. histicola* (*P. histicola* fed), or culture supernatant from a *P. histicola* culture (*P. histicola* Culture Supernatant fed).

DETAILED DESCRIPTION

This document provides methods and materials related to *P. histicola* preparations. For example, this document provides compositions containing *P. histicola* (e.g., live *P. histicola*, killed *P. histicola*, *P. histicola* components, or lysed *P. histicola*). Such compositions can contain any amount of *P. histicola* or *P. histicola* components. In some cases, a composition provided herein can contain *P. histicola* (e.g., live or killed *P. histicola*) or *P. histicola* components in an amount such that between 0.001 and 100 percent (e.g., between 1 and 95 percent, between 10 and 95 percent, between 25 and 95 percent, between 50 and 95 percent, between 20 and 80 percent, between 50 and 95 percent, between 60 and 95 percent, between 70 and 95 percent, between 80 and 95 percent, between 90 and 95 percent, between 95 and 99 percent, between 50 and 100 percent, between 60 and 100 percent, between 70 and 100 percent, between 80 and 100 percent, between 90 and 100 percent, or between 95 and 100 percent), by weight, of the composition can be *P. histicola* or *P. histicola* components. In some cases, a composition provided herein can contain between about $10^3$ and $10^8$ live *P. histicola* microorganisms.

In some cases, a composition provided herein can contain *P. histicola* (e.g., live *P. histicola* microorganisms) in the amounts and dosages as described elsewhere for probiotic bacteria (U.S. Patent Application Publication No. 2008/0241226; see, e.g., paragraphs [0049-0103]). In addition, a composition provided herein containing *P. histicola* (e.g., live *P. histicola* microorganisms) can be administered as described elsewhere for probiotic bacteria (U.S. Patent Application Publication No. 2008/0241226; see, e.g., paragraphs [0049-0103]).

Live *P. histicola* microorganisms can be obtained from the digestive system of any appropriate mammal (e.g., a human). For example, *P. histicola* microorganisms can be isolated from small intestinal mucosa (e.g., a small bowel biopsy or aspirate sample) of a human (e.g., a human patient diagnosed with celiac disease). *P. histicola* strains can be identified via 16S rRNA PCR using standard 16S rRNA primers. The 16S rRNA sequence used to identify *P. histicola* can be as set forth in FIG. 10. In some cases, *P. histicola* microorganisms can be obtained from the ARS Culture Collection (NRRL accession number NRRL B-50329, deposited Oct. 28, 2009).

Any appropriate method can be used to obtain a culture of *P. histicola* microorganisms. For example, standard microbial culturing techniques can be used to obtain *P. histicola* or *P. histicola* components. In general, *P. histicola* microorganisms can be cultured in broth containing milk (e.g., skim milk) to obtain a culture containing greater than 1×10$^8$ *P. histicola* per mL of broth. The *P. histicola* microorganisms can be removed from the broth via centrifugation. Once obtained, the live *P. histicola* microorganisms can be formulated into a medicament or nutritional supplement composition for administration to a mammal (e.g., a human), can be added to a food product for consumption, or can be frozen for later use. In some cases, the obtained *P. histicola* microorganisms can be treated (e.g., chemical treatment, repeated freeze-thaw cycles, antibiotic treatment, or fixation treatment such a formalin treatment) to obtain a composition of killed or lysed *P. histicola* microorganisms or can be processed (e.g., lysed followed by fractionation) to obtain a composition of *P. histicola* components.

In some cases, a *P. histicola* preparation, which can be stored frozen in 2× skim milk, can be thawed and grown on CDC Anaerobe Laked Sheep Blood Agar with kanamycin and vancomycin (KV) (Becton, Dickson and Company, Sparks, Md., product number 221846) in an anaerobe jar with AnaeroPack System (product number 10-01, Mitsubishi Gas Chemical America, Inc., New York, N.Y.). The culture can be incubated at 35-37° C. for at least 48 hours.

A composition containing *P. histicola* or *P. histicola* components can be in the form of an oral medicament or nutritional supplement. For example, compositions containing *P. histicola* or *P. histicola* components can be in the form of a pill, tablet, powder, liquid, or capsule. Tablets or capsules can be prepared by conventional means with pharmaceutically acceptable excipients such as binding agents, fillers, lubricants, disintegrants, or wetting agents. The tablets can be coated by methods known in the art. In some cases, a composition containing P. histicola or P. histicola components can be formulated such that live or killed P. histicola or P. histicola components are encapsulated for release within the intestines of a mammal. Liquid preparations for oral administration can take the form of, for example, solutions, syrups, or suspension, or they can be presented as a dry product for constitution with saline or other suitable liquid vehicle before use. In some cases, a composition provided herein containing P. histicola (e.g., live P. histicola microorganisms) can be in a dosage form as described elsewhere (U.S. Patent Application Publication No. 2008/0241226; see, e.g., paragraphs [0129-0135]). For example, a composition provided herein can be in the form of a food product formulated to contain P. histicola (e.g., live P. histicola microorganisms) or P. histicola components. Examples of such food products include, without limitation, milk (e.g., acidified milk), yogurt, milk powder, tea, juice, beverages, candies, chocolates, chewable bars, cookies, wafers, crackers, cereals, treats, and combinations thereof.

A composition containing P. histicola or P. histicola components can contain other ingredients such as buffers, radical scavengers, antioxidants, reducing agents, or mixtures thereof. For example, a composition containing live P. histicola can be formulated to contain botanicals, vitamins, minerals, or combinations thereof. In some cases, a composition provided herein containing P. histicola (e.g., live P. histicola microorganisms) can contain other ingredients as described elsewhere (U.S. Patent Application Publication No. 2008/0241226; see, e.g., paragraphs [0104-0128]).

In some cases, a composition containing P. histicola or P. histicola components can contain a pharmaceutically acceptable carrier for administration to a mammal, including, without limitation, sterile aqueous or non-aqueous solutions, suspensions, and emulsions. Examples of non-aqueous solvents include, without limitation, propylene glycol, polyethylene glycol, vegetable oils, and organic esters. Aqueous carriers include, without limitation, water, alcohol, saline, and buffered solutions. Pharmaceutically acceptable carriers also can include physiologically acceptable aqueous vehicles (e.g., physiological saline) or other known carriers for oral administration.

This document also provides methods and materials for using a composition containing P. histicola or P. histicola components as an anti-inflammatory agent. In some cases, a composition containing P. histicola or P. histicola components can be used to treat autoimmune conditions such as arthritis, multiple sclerosis, systemic lupus erythematosus (SLE), type 1 diabetes (T1D), and Crohn's disease. In some cases, a composition containing P. histicola or P. histicola components can be used as a nutritional supplement to supplement a mammal's diet with bacterial organisms having the ability to reduce the severity or development of an autoimmune condition. Examples of mammals include, without limitation, humans, monkeys, dogs, cats, cows, horses, pigs, and sheep.

Any amount of a composition containing P. histicola or P. histicola components can be administered to a mammal. The dosages of P. histicola (e.g., live or killed P. histicola) or P. histicola components can depend on many factors including the desired results. Typically, the amount of P. histicola (e.g., live or killed P. histicola) or P. histicola components contained within a single dose can be an amount that effectively exhibits anti-inflammatory activity within the mammal. For example, a composition containing live P. histicola can be formulated in a dose such that a mammal receives between about $10^3$ and $10^8$ live P. histicola microorganisms.

The final pH of a composition P. histicola (e.g., live or killed P. histicola) or P. histicola components can be between about 3.5 and about 9.5 (e.g., between about 4.0 and about 9.0; between about 4.5 and about 9.0; between about 4.5 and about 8.5; between about 5.0 and about 8.5; or between about 6.5 and about 8.0). To obtain such a pH, the pH of the composition can be adjusted using a pH-adjusting agent, for example. It will be appreciated that pH adjustment can be accomplished with any of a wide variety of acids should the composition have a pH that is too high (e.g., greater than 10.0 before adjustment). Likewise, pH adjustment can be accomplished with any of a wide variety of bases should the composition have a pH that is too low (e.g., less than 3.0 before adjustment).

The invention will be further described in the following examples, which do not limit the scope of the invention described in the claims.

EXAMPLES

Example 1—Use of P. histicola to Reduce Disease Symptoms in an Animal Model of Multiple Sclerosis The following was performed to demonstrate that an ongoing inflammatory condition such as multiple sclerosis (MS), a demyelinating autoimmune disease of the central nervous system, can be treated by a systemic anti-inflammatory response induced by P. histicola. Transgenic (Tg) mice expressing human HLA class II genes (HLA-DR3DQ8) associated with MS can be used as an animal model to study MS. HLA-DR3DQ8 mice develop severe inflammation and demyelination in CNS mimicking human disease. As demonstrated herein, feeding P. histicola to DR3.DQ8.AEo mice after induction of experimental autoimmune encephalomyelitis (EAE) reduced disease incidence and severity. Control bacteria such as C. sputigena or E. coli, however, had not effect on disease incidence or severity indicating that the suppressive effect is unique to P. histicola. In addition, P. histicola treated mice exhibited a decrease in myelin antigen specific T cell responses as well as a decrease in the level of IL-17, an inflammatory cytokine. Treatment with P. histicola also resulted in increases in levels of IL-10, an anti-inflammatory cytokine.

Methods

Transgenic (Tg) Mice

HLA-DQ8 (DQA1*0103, DQB1*0302), HLA-DR3 (DRB1*0301), and HLA-DR3/DQ8 Tg mice were produced as described elsewhere (Das et al., Hum. Immunol., 61:279-289 (2000); Bradley et al., J. Clin. Invest., 100:2227-2234 (1997); and Strauss et al., Immunogenetics, 40:104-108 (1994)). Briefly, HLA class II transgenes were introduced into (B6×SWR)F$_1$ fertilized eggs. Positive offspring were backcrossed to B10.M mice for several generations. HLA transgenic mice were then mated to class II-deficient (Aβ°) mice and intercrossed to generate the HLA transgenic lines. To generate double transgenic mice, single transgenic DR3.Aβ° mice were mated with DQ8.Aβ° Tg lines to produce HLA-DR3/DQ8 Tg lines. These HLA class-II Tg mice were mated with MHC-II$^{\Delta/\Delta}$ (AE° mice (Taneja et al., J. Immunol., 181:2869-2877 (2008)) to generate AE°.DQ8. AE°.DR3 and AE°.DR3.DQ8 mice. Transgene negative littermates were used as controls. All mice were bred and maintained in the pathogen free environment according to National Institutes of Health and institutional guidelines. All experiments were approved by the institutional committee.

Flow Cytometry

Expression of HLA-DR and HLA-DQ molecules on PBLs, lymph node cells (LNCs), and splenocytes were analyzed by flow cytometry using monoclonal antibodies (mAbs) L227 and IVD12, specific for HLA-DR and HLA-DQ (Lampson et al., J. Immunol., (Baltimore, Md.: 1950) 125:293-299), respectively, as described elsewhere (Bradley et al., J. Clin. Invest., 100:2227-2234 (1997)). Surface expression of CD4 (GK1.5), CD8 (53.6.72), a B cell marker (CD45R (RA3-6B2)), a DC cell marker (CD11c (HL3)), a monocyte/macrophage cell marker (CD11b (M1/70)), and NK cell markers (PK136), CD25 (PC61), CD44 (IM7), and CD45RB (16A)) were analyzed using fluorescent conjugated mAb from BD Biosciences (San Jose, USA).

Polypeptide

Twenty-amino acid-long synthetic peptide proteolipid protein $PLP_{91\text{-}110}$ (YTTGAVRQIFGDYKTTICGK; SEQ ID NO:3; See, GenBank Accession No. NP_000524 for full length 277 amino acid PLP polypeptide) was synthesized at the peptide core facility of Mayo Clinic, Rochester, Minn.

Immunization and T Cell Proliferation Assay

Mice were immunized subcutaneously with $PLP_{91\text{-}110}$ (100 μg) polypeptide, emulsified in CFA (1:1) containing 100 μg of *Mycobacterium tuberculosis* H37Ra (Difco, Detroit, Mich.) as described elsewhere (Mangalam et al., J. Immunol., 182: 5131-5139 (2009)). Some immunized mice were sacrificed 10 days after immunization, and draining lymph nodes were removed and challenged in vitro with antigen (Das et al., Hum. Immunol., 61:279-289 (2000)). The results are presented as stimulation indices (CPM of test sample/CPM of the control).

Disease Induction

For disease induction, 12-14 weeks old Tg mice were immunized subcutaneously in both flanks with 100 μg of $PLP_{91\text{-}110}$ emulsified in CFA containing *Mycobacterium tuberculosis* H37Ra (400 μg/mice) (Mangalam et al., J. Immunol., 182: 5131-5139 (2009)). Pertussis toxin (Sigma Chemicals, St. Louis, Mo., USA; 100 ng) was injected i.v. at day 0 and 2, post immunization. Mice were observed daily for clinical symptoms, and disease severity was scored as follows: 0, normal; 1, loss of tail tone; 2, hind limb weakness; 3, hind limb paralysis; 4, hind limb paralysis and forelimb paralysis or weakness; and 5, moribundity/death. Mice of both sexes were used.

Treatment with *Prevotella* or Other Commensal Bacteria

To test therapeutic potential of *P. histicola*, mice were first immunized with myelin antigen (PLP91-110). One week after induction of EAE, mice were treated with bacteria by oral gavage. Commensal Gram negative, anaerobic bacteria (*Capnocytophagia sputigena* or *E. coli*) also were tested as a treatment option. DR3DQ8 mice received *P. histicola* or *C. sputigena* or *E. coli* or medium alone starting day 7 post-immunization and every other day for a total of seven doses. Mice were followed for weight loss, disease incidence, duration, and severity for four weeks post-immunization.

Cytokine Analysis

For cytokine analysis, supernatants from different groups were collected from culture 48 hours after polypeptide stimulation. The concentration of cytokines (IL-1, IL-2, IL-4, IL-5, IL-6, IL-10, IL-12, IL-13, IL-17, GM-CSF, IFN-γ, TNF-α, MCP-1, MIP-1α, MIP-1β, etc.) in the supernatant was measured using 23-plex BioPlex cytokine bead arrays (BioRad) and sandwich ELISA (TGF-β, IL-22, and IL-23) using pairs of relevant anti-cytokine monoclonal antibodies according to the manufacturer's protocol (Pharmingen, San Diego, Calif., USA).

Results

Isolation of Commensal Bacteria and their Effect on $PLP_{91\text{-}110}$ Induced EAE in HLA-DR3.DQ8 Double Transgenic Mice Commensal bacteria were isolated from small intestinal mucosa of human patients and tested their ability to modulate the disease process of EAE. *Prevotella histicola*, anaerobic, Gram-negative, non-pigmented bacteria, were isolated and tested for the ability to modulate $PLP_{91\text{-}110}$-induced EAE in double transgenic mice. EAE was induced in HLA-DR3DQ8 transgenic mice by immunization with $PLP_{91\text{-}110}$ emulsified in CFA at 1:1 ratio. These mice also received pertussis toxin at day 0 and day 2 post-immunization. To test therapeutic potential of *Prevotella histicola*, mice were treated with bacteria (oral gavage) 7 day post immunization. DR3DQ8 mice received either *Prevotella histicola* or medium staring day 7 post-immunization and every other day for a total of 7 doses. Mice were followed for weight loss, disease incidence, duration and severity for 4 weeks post-immunization. *Capnocytophagia sputigena* or *E. coli* were used as control commensal bacteria.

Figure 1:
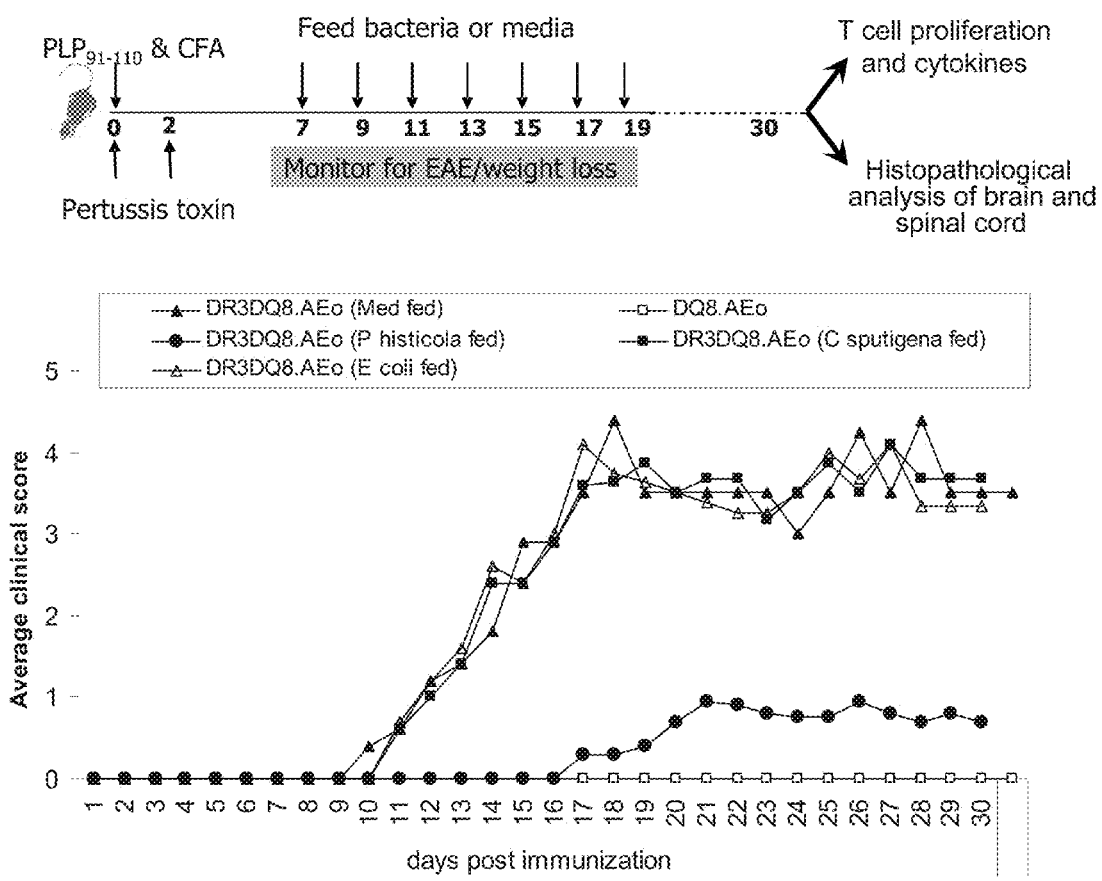
FIG. 1. Modulation of EAE by *Prevotella histicola*. Treatment with *P. histicola* protected a majority of DR3DQ8 mice from developing EAE, while medium fed control mice or DR3DQ8 mice treated with control commensal bacteria (*Capnocytophagia sputigena* or *E. coli*) exhibited 100% disease incidence, thereby indicating that *P. histicola* have an immunomodulatory effect. HLA-DR3DQ8 or DQ8 control Tg mice were immunized with $PLP_{91-110}$ myelin antigen emulsified in CFA. Pertussis toxin was given at day 0 and 2 post-immunization. Seven days post immunization mice were gavaged on alternate days either with *P. histicola* or *Capnocytophagia sputigena* or *E. coli* ($2 \times 10^9$ CFU in 100 µL of trypticase soy broth (TSB) culture media) or medium for 7 doses. Mice were monitored daily for development of EAE and scored using standard EAE scoring criteria as described elsewhere (Mangalam et al., *J. Immunol.*, 182(8): 5131-9 (2009)). At the end of treatment, tissue and sera were collected from the mice for further analysis. No immunomodulatory effect was observed with other tested human or mouse commensal bacteria.

*Prevotella histicola* fed mice exhibited significantly reduced disease incidence as only 25% (4/20) mice develop EAE as compared 100% disease incidence in medium fed (sham treated) DR3DQ8 mice (FIG. 1 and Table 1). Treatment with *C. sputigena* or *E. coli* had no effect on development or severity of disease in DR3DQ8 mice, indicating that only *P. histicola* have immunomodulatory effect. No disease was observed in DQ8 single transgenic mice. Further, disease onset in DR3DQ8 mice in *P. histicola* treated group was significantly delayed in bacteria treated mice.

TABLE I

Effect of bacteria on $PLP_{91\text{-}110}$ induced EAE in HLA Tg mice[a]

| Mouse strain | Disease incidence (%) | Mean onset of disease ± SD | Number of mice with maximum severity score | | | | |
|---|---|---|---|---|---|---|---|
| | | | 1 | 2 | 3 | 4 | 5 |
| DQ8.AE° (Medium) | 0/10 (0%) | — | — | — | — | — | — |
| DR3.DQ8.AE° (Medium) | 20/20 (100%) | 10 ± 1 | — | — | 4 | 10 | 6 |
| DR3.DQ8.AE° (*P histicola*) | 4/20 (25%) | 18 ± 2 | — | 1 | 3 | — | — |
| DR3.DQ8.AE° (*C sputigena*) | 10/10 (100%) | 13 ± 2 | — | 1 | 5 | 2 | 3 |
| DR3.DQ8.AE° (*E coli*) | 10/10 (100%) | 15.7 ± 2.5 | — | — | 6 | 1 | 4 |

[a]mice were immunized with 100 μg of PLP peptide/400 μg Mtb in CFA, and Ptx was administered at 0 and 48 hours post immunization. Mice were scored daily for disease. The data is from three experiments combined.

Effect of *Prevotella histicola* on Antigen Specific T Cell Proliferation

Figure 2:
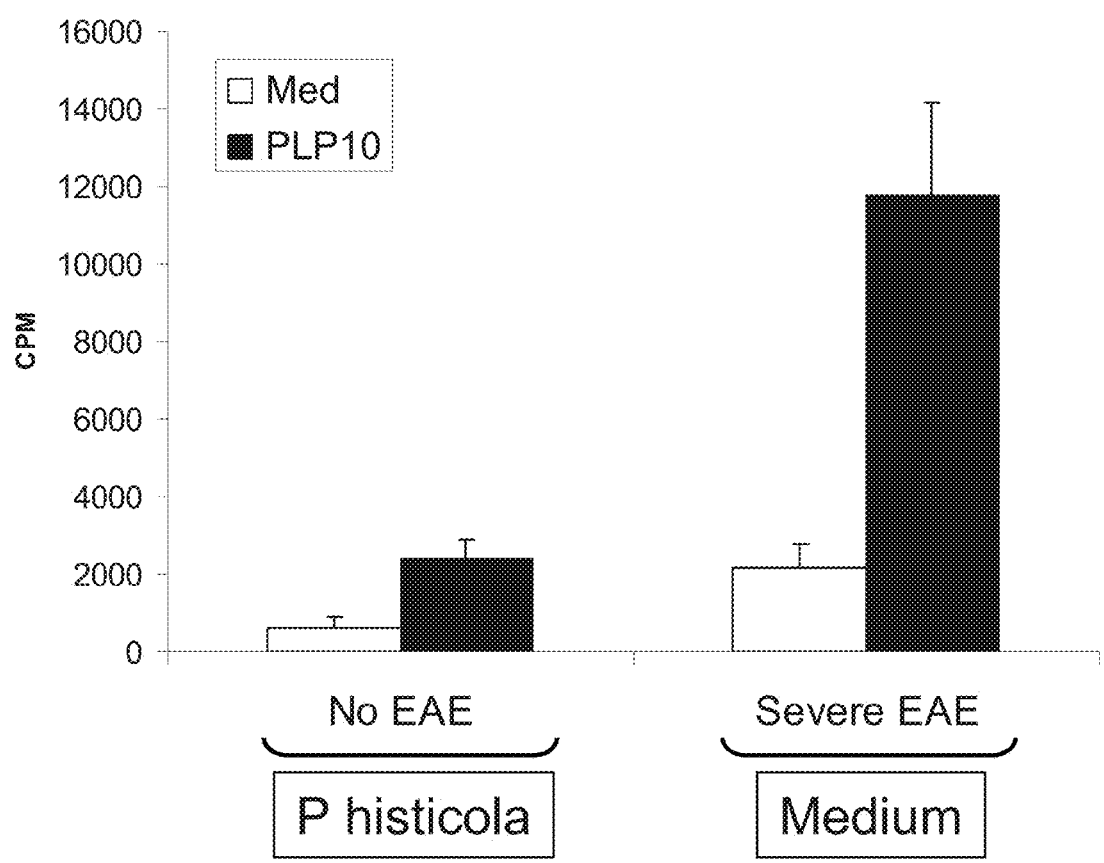
FIG. 2. *P. histicola* treated DR3DQ8 mice exhibited reduced $PLP_{91-110}$ specific T cell proliferation as compared to sham treated mice. Splenocytes were collected from mice immunized with PLP and treated with *P. histicola* or medium (sham) and were stimulated in vitro with the $PLP_{91-110}$ polypeptide.

To determine if this protective effect of *P. histicola* is due to down-regulation of antigen specific T cell responses, splenocytes were isolated from mice treated with bacteria or medium, and stimulated with $PLP_{91\text{-}110}$ peptide. An antigen specific T cell response was suppressed in DR3DQ8 mice treated *P. histicola* as compared to sham treated mice (FIG. 2).

Effect of *P. histicola* on Cytokine and Chemokine Production

The levels of cytokine and chemokines between bacteria fed and medium fed mice were compared to determine if *P.*

Figure 3:
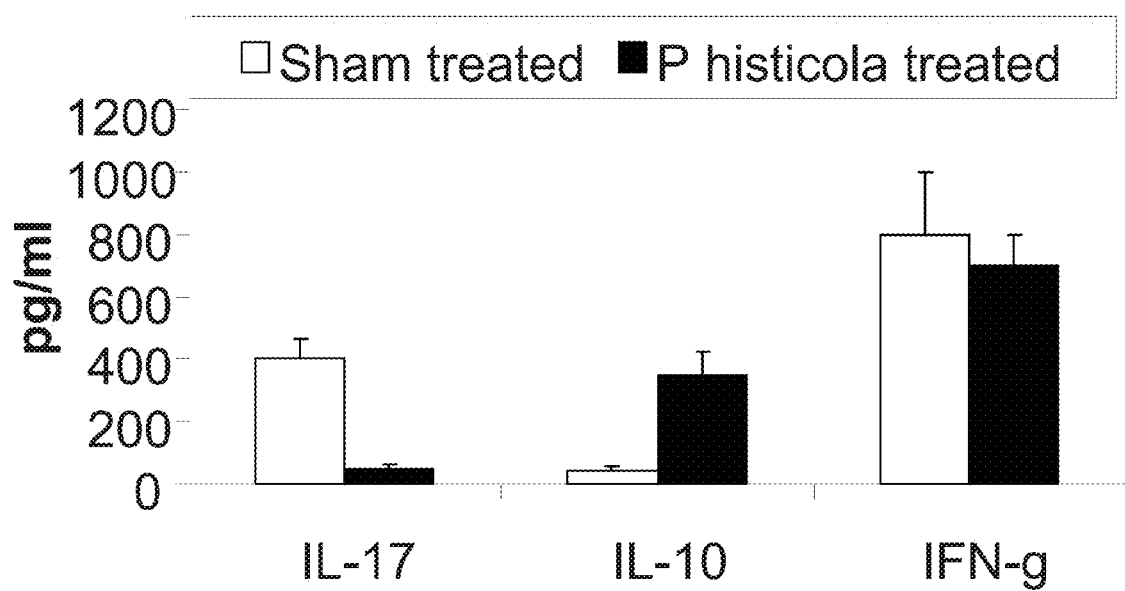
FIG. 3. *P. histicola* treated DR3DQ8 mice exhibited reduced level of IL-17 and increased levels of IL-10 as compared to sham treated mice. Levels of IFN-γ were not different between the two groups of mice.

*histicola* protected mice from EAE by modulating levels of pro and anti-inflammatory chemical mediators. Splenocytes from bacteria fed mice produced less IL-17, a pro-inflammatory cytokine) on stimulation with PLP, while levels of IL-10, an anti-inflammatory cytokine), were increased (FIG. 3). Surprisingly, levels of IFN-γ were not significantly different between the two groups.

Figure 4A:
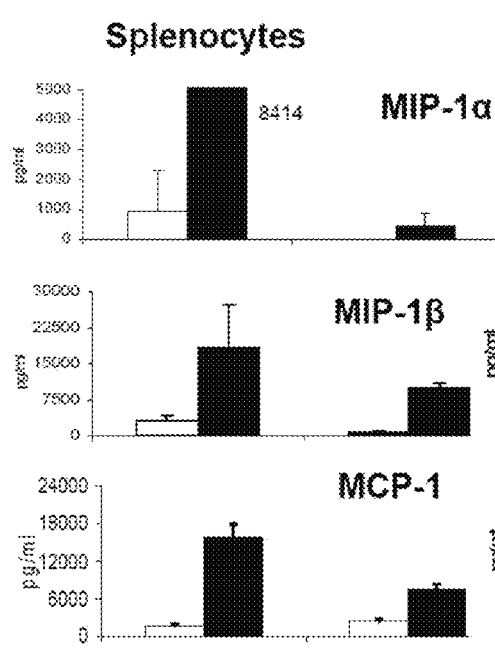
FIGS. 4A-B.
Figure 4B:
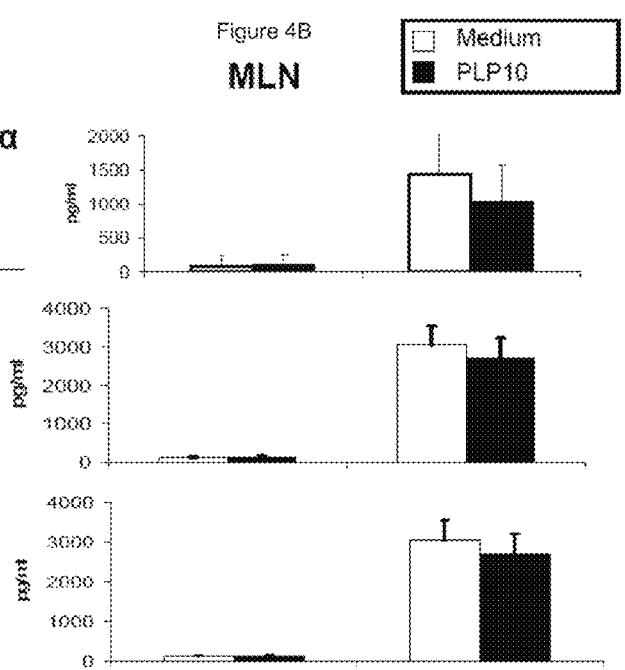

Cells from splenocytes of mice protected from EAE (*P. histicola* treated mice) produced reduced levels of MIP-1α, MIP-1β, and MCP-1 as compared to levels observed in mice with EAE (medium treated) (FIG. 4A). At the same time, the levels of these chemokines in mesenteric lymph node cells were significantly higher in protected mice (*P. histicola* treated mice) as compared to mice with EAE (FIG. 4B).

These results demonstrate that *P. histicola* can have an immuno-modulatory effect that suppresses proliferation of IL-17-secreting Th17 cells and increases production of IL-10, an immunoregulatory cytokine. While not being limited to any particular mode of action, *P. histicola* may modulate EAE in HLA-DR3DQ8 transgenic mice by suppressing production of chemokines in encephalitogenic CD4 T cells, thereby inhibiting migration of pathogenic cells to CNS.

In another experiment, the frequencies of regulatory T cells (e.g., CD4$^+$FoxP3$^+$ regulatory T cells) and tolerogenic dendritic cells (e.g., CD11b$^+$ CD11c$^+$ CD103$^+$ tolerogenic DCs) were assessed in the HLA-DR3DQ8 transgenic mouse model of EAE using sham treated mice and *P. histicola* treated mice. Briefly, AEo.DRB1*0301/DQ8 (HLA-DR3DQ8) Tg mice were immunized with PLP$_{91-110}$ myelin antigen emulsified in CFA. Pertussis toxin was given at day 0 and 2 post-immunization. Seven days post immunization mice were gavaged on alternate days with either *P. histicola* (2×10$^9$ CFU in 100 μL of TSB culture media) or medium for seven doses. Mice were monitored daily for development of EAE and scored using standard EAE scoring criteria as described elsewhere (Mangalam et al., *J. Immunol.*, 182(8): 5131-9 (2009)). Splenocytes and cells from mesenteric lymph node (MLN) were used for analysis of T regulatory cells and for analysis of CD11b$^+$ CD11c$^+$ CD103$^+$ tolerogenic DCs.

A plot was generated from CD4 gated cells, revealing the percent CD4$^+$FoxP3$^+$ cells in spleen and MLN (FIG. 11). *P. histicola* treated HLA-DR3DQ8 mice exhibited an increased frequency of CD4$^+$FoxP3$^+$ regulatory T cells in spleen (80% vs. 24%) and mesenteric lymph node (54% vs. 43%) as compared to the frequencies observed in sham treated mice (FIG. 11). A plot also was generated from CD11b$^+$ and CD11c$^+$ gated cells, revealing the percent CD11b$^+$ CD11c$^+$ CD103$^+$ cells in spleen and MLN (FIG. 12). *P. histicola* treated HLA-DR3DQ8 mice exhibited an increased frequency of CD11b$^+$ CD11c$^+$ CD103$^+$ tolerogenic DCs in spleen (22% vs. 6%) and mesenteric lymph node (52% vs. 45%) as compared to the frequencies observed in sham treated mice (FIG. 12).

These results demonstrate that treatment with *P. histicola* leads to an increase in the frequency of regulatory T cells and tolerogenic dendritic cells. These results also demonstrate that *P. histicola* can modulate EAE in DR3DQ8 Tg mice by modulation of a cytokines, regulatory T cell, and regulatory dendritic cell network. In addition, suppressive dendritic cells can be responsible for conversion of T cells to a regulatory phenotype. The regulatory T cells of treated mice can migrate from lamina propria to periphery, thus modulating overall immune response.

Example 2—Use of *P. histicola* to Reduce Disease Symptoms in an Animal Model of Arthritis The following was performed to demonstrate that an ongoing inflammatory condition such as rheumatoid arthritis (RA), a chronic inflammatory autoimmune disease of the joints, can be treated by a systemic anti-inflammatory response induced by *P. histicola*. Transgenic (Tg) mice expressing human HLA class II genes (HLA-DQ8) associated with RA can be used as an animal model to study immunopathogenesis of RA. HLA transgenic mice expressing HLA-DQ8 (HLA-DQA1*0301/DQB1*0302) were highly susceptible to collagen-induced arthritis (CIA), an animal model of human RA (Taneja et al. *J. Immunol.*, 181:2869-7 (2008)). As demonstrated herein, feeding *P. histicola* to DQ8.AEo mice after induction of collagen induced arthritis (CIA) reduced disease incidence and severity. The group of mice receiving medium only exhibited no effect on disease incidence or severity indicating that *P. histicola* has a disease suppressive effect. In addition, *P. histicola* treated mice exhibited a decrease in the level of pro-inflammatory and immunomodulatory cytokines. Treatment with *P. histicola* also resulted in a decrease in the levels of anti-type II collagen (CII) specific antibodies.

Transgenic (Tg) Mice

DQ8.Abo mice were generated as described previously. These mice were mated with MHC-II$^{\Delta/\Delta}$ (AE° mice (Taneja et al., *J. Immunol.*, 181:2869-2877 (2008)) to generate AE°.DQ8 mice. All mice were bred and maintained in the pathogen free environment according to appropriate guidelines. All experiments were approved by the institutional committee.

Flow Cytometry

Expression of HLA-DQ molecules on PBLs, lymph node cells (LNCs), and splenocytes were analyzed by flow cytometry using monoclonal antibodies (mAbs) IVD12, specific for HLA-DQ (Lampson et al., *J. Immunol.*, (Baltimore, Md.: 1950) 125:293-299), respectively, as described elsewhere (Bradley et al., *J. Clin. Invest.*, 100:2227-2234 (1997)). Surface expression of CD4 (GK1.5), CD8 (53.6.72), a B cell marker (CD45R (RA3-6B2)), a DC cell marker (CD11c (HL3)), a monocyte/macrophage cell marker (CD11b (M1/70)), GITR [Glucocorticoid-induced Tumor necrosis factor (TNF) receptor family-Related] (DTA-1), and CD103 (M290) were analyzed using fluorescent conjugated mAb from BD Biosciences (San Jose, USA).

Induction and Evaluation of CIA

Pure native chick type II collagen was obtained by multiple-step purification as described elsewhere (Griffiths et al., *Arthritis Rheum.*, 24:781-789 (1981)). Tg mice and negative littermates were immunized with chick CII as described elsewhere for CIA the protocol (Taneja et al., *Arthritis Rheum.*, 56:69-78 (2007)). Mice were monitored for the onset and progression of CIA from 3 to 12 weeks post-immunization. The arthritic severity of mice was evaluated as described elsewhere with a grading system for each paw from 0 to 3 (Wooley, *J. Exp. Med.*, 154:688-700 (1981)). The mean arthritic score was determined using arthritic animals only.

Autoantibodies

Levels of anti-chick and anti-mouse CII IgG Abs were measured in sera obtained 35 days following CII immunization by a standard ELISA and are shown as OD. Briefly, microtiter plates were coated overnight with CII (6 μg/well in KPO$_4$ (pH 7.6)) at 4° C., washed, and blocked with 1% BSA in PBS/0.05% Tween 20. Sera were added in 4-fold dilution (1/100 to 1/65,000) and incubated overnight at 4° C.

The plates were washed, and peroxidase-conjugated goat anti-mouse IgG (Organon Teknika) was added for another overnight incubation at 4° C. After washing, O-phenylenediamine was added, and the colorimetric change was measured at 410 nm.

T Cell Proliferation Assay

Mice were immunized with 200 µg of CII emulsified 1:1 in CFA (Difco) intradermally at the base of the tail and in one hind footpad. Ten days post-immunization, draining lymph nodes/spleen were removed and cultured in vitro. Lymph node cells (LNCs, $1 \times 10^6$) were cultured in HEPES-buffered RPMI 1640 containing 5% heat-inactivated horse serum and streptomycin and penicillin in 96-well flat-bottom tissue culture plates. Cells were challenged by adding 100 µL of RPMI 1640 medium (negative control), Con A (20 µg/mL, positive control), and native collagen (50 µg/mL). To determine CD4-mediated response, GK1.5 (anti-CD4) Ab was used for blocking. The cells were incubated for 48 hours at 37° C. During the last 18 hours, the cells were pulsed with [$^3$H]thymidine, and the tritium incorporation was determined by liquid scintillation counting. Results are calculated as Δ cpm (i.e., mean cpm of triplicate cultures containing Ag−mean cpm of medium).

Cytokines

Cytokines (IL-1α, IL-1β, IL-5, IL-6, IL-10, IL-12p40, IL-13, IL-17, TNFα, and IFNγ) were measured using the Bio-Plex protein array system with the mouse cytokine 23-plex panel as per the manufacturer's instructions and analyzed with Bio-Plex manager 2.0 software (Bio-Rad Laboratories).

Results

Modulation of Collagen-Induced Arthritis (CIA) by *Prevotella Histicola*.

Immunization of HLA-DQ8.AEo mice with type II collagen (CII) leads to development of collagen-induced arthritis, a model for rheumatoid arthritis (Taneja et al., *J. Immunol.*, 56:69-78 (2007)). Treatment with *P. histicola* protected DQ8.AEo mice from developing arthritis (FIG. 5). Three groups of mice were included: (1) mice immunized with CII/CFA and treated with medium, (2) mice immunized with CII and treated with *P. histicola*, and (3) mice immunized with *P. histicola* without CII, a control group. Ten days post immunization mice were gavaged three times per week with *P. histicola* ($2 \times 10^9$ CFU in 100 µL of TSB culture media) for up to 7 weeks. Group 1 and group 2 mice were boosted with CII/IFA in $6^{th}$ week. Mice were monitored for arthritis for up to 10 weeks. Mice immunized with CII and treated with *P. histicola* exhibited a dramatic decrease in disease incidence as well as milder disease. Mice only given *P. histicola* did not develop any arthritis. Mice receiving medium only had no effect on CIA.

Effect of *P histicola* on Auto-Antibodies Levels and T Cell Proliferation

*P. histicola* treated mice exhibited reduced humoral antigen-specific response. Anti-CII antibodies in sera collected before and after treatment with *P. histicola* exhibited a reduction in antibodies (FIG. 6A). Anti-CII antibodies were tested by ELISA. T cell proliferation to CII in vitro did not exhibit any significant reduction in *P. histicola* vs. medium treated mice. Only *P. histicola* gavaged mice did not exhibit any antigen (CII)-specific response (FIG. 6B).

Effect of *P. histicola* on Cytokine Production

All pro-inflammatory and immunomodulatory cytokines produced in response to CII were reduced in *P. histicola* treated mice as compared to medium fed (control) mice (FIG. 7). Cytokines were measured from serum of mice by using multiplex array system.

Effect of *P. histicola* on Regulatory T Cells and Regulatory Dendritic Cells (DCs) in Splenocytes and Lamina Propria Mice treated with *P. histicola* exhibited a higher number of CD4$^+$GITR$^+$ T regulatory cells and CD11c$^+$CD103$^+$ dendritic cells in splenocytes as compared to mice receiving medium only (FIG. 8). Treatment with *P. histicola* also resulted in an increase in regulatory dendritic cells, CD11c$^+$CD103$^+$ in lamina propria (FIG. 9).

These results demonstrate that *P. histicola* can have an immunomodulatory effect that reduces the disease incidence and severity of CIA in DQ8 Tg mice. While not being limited to any particular mode of action, *P. histicola* may modulate CIA in DQ8 Tg mice by modulation of cytokines, regulatory T cells, and regulatory dendritic cells network.

In another experiment, regulatory T cell (e.g., CD4$^+$FoxP3$^+$ regulatory T cells) and tolerogenic dendritic cell (e.g., CD11b$^+$ CD11c$^+$ CD103$^+$ tolerogenic DCs) responses were assessed in the AEoDRB1*0401/DQ8 mouse model of arthritis using sham treated mice and *P. histicola* treated mice. Briefly, AEoDRB1*0401/DQ8 mice were sham treated or treated with *P. histicola* three times on alternative days before being immunized with 100 µg of type II collagen (CII) emulsified in CFA and four times on alternative days after immunization. Splenocytes were used to isolate DCs (adherent cells) and CD4$^+$ T cells by staining with conjugated antibodies and FAC sorting. Cells were used at 99% purity.

To assess proliferation, CD4$^+$ cells from sham treated mice were cultured in vitro with DCs from sham treated or *P. histicola* treated mice in the presence or absence of CII. Similarly, CD4$^+$ cells isolated from spleens of *P. histicola* treated mice were cultured with DCs from sham treated or *P. histicola* treated mice in the absence or presence of CII. A histogram plot was generated from the proliferation results from three mice (FIG. 13A). *P. histicola* treated CD4$^+$ cells generated a good T cell response to CII when it was presented by sham DCs, but not when presented by DCs from *P. histicola* treated mice (FIG. 13A). CD4$^+$ cells from sham treated cultured with DCs from *P. histicola* treated mice did not show any proliferation, suggesting *P. histicola* treated DCs are suppressive (FIG. 13A).

The supernatants from the cultures assessed in FIG. 13A were assessed to IL-17 and IL-10 levels. Sham CD4$^+$ and DC cultures produced more IL-17 than IL-10, while cultures using in vivo *P. histicola* treated DCs cultured with CD4$^+$ cells from sham and *P. histicola* treated mice produced much higher amounts of IL-10 than IL-17 (FIG. 13B). These results demonstrate that *P. histicola* treatment can have an immuno-modulatory effect that suppresses proliferation of IL-17-secreting Th17 cells and increases production of IL-10, an immunoregulatory cytokine. The increase in IL-10 production can be due to an increase in T regulatory cells or suppressive DCs and may one mechanism of protection.

The frequencies of CD4$^+$CD25$^+$FoxP3$^+$ regulatory T cells in sham treated or *P. histicola* treated HLA-DRB1*0401/DQ8 mice were assessed. Briefly, mice were treated with *P. histicola* as described with respect to FIG. 13, and splenocytes and cells from lamina propria were used for analysis of T regulatory cells. A plot was generated from CD4$^+$ gated cells, revealing the percent of CD4$^+$CD25$^+$FoxP3$^+$ cells in spleen and lamina propria (FIG. 14). *P. histicola* treated HLA-DRB1*0401/DQ8 mice exhibited an increased frequency of CD4$^+$CD25$^+$FoxP3$^+$ regulatory T cells in spleen and lamina propria as compared to the frequencies observed in sham treated mice (FIG. 14). These regulatory T cells may be responsible for the produced IL-10 as shown in FIG. 13B.

These results demonstrate that *P. histicola* can modulate cytokine production in transgenic mice via regulatory T and suppressive dendritic cells. Suppressive dendritic cells can be responsible for conversion of T cells to regulatory phenotype. The regulatory T cells of treated mice can migrate from lamina propria to periphery, thus modulating overall immune response.

Example 3—Use of *P. histicola* and *P. histicola* Culture Supernatants to Reduce Disease Symptoms in an Animal Model of Multiple Sclerosis The following was performed to demonstrate that *P. histicola* and *P. histicola* culture supernatants can modulate EAE. HLA-DR3DQ8 Tg mice were immunized with $PLP_{91-110}$ myelin antigen emulsified in CFA. Pertussis toxin was given at day 0 and 2 post-immunization. Seven days post immunization mice were gavaged on alternate days either with live *P. histicola* or culture supernatant of *P. histicola* or medium only for seven doses. *P. histicola* was grown in TSB media as described herein, and the culture supernatant of *P. histicola* was collected by centrifuging the *P. histicola* culture. Mice were monitored daily for development of EAE and scored using standard EAE scoring criteria as described elsewhere (Mangalam et al., *J. Immunol.*, 182(8):5131-9 (2009)).

Treatment of DR3/DQ8 mice with media in which *P. histicola* were cultured resulted in a protective effect with only 50% of mice developing EAE compared to 100% incidence in control mice (media fed) mice (FIG. 15). *P. histicola* treated HLA-DR3DQ8 mice were used as positive control and exhibited a strong protective effect (FIG. 15). These results indicate that live *P. histicola* and culture supernatants of *P. histicola* can be used to reduce the severity of symptoms of inflammatory conditions and autoimmune conditions. In addition, these results demonstrate that culture supernatants of *P. histicola* may exhibit their immunomodulatory effect via products secreted by *P. histicola*, bacterial lysates present in the culture supernatant, or both.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of stimulating an anti-inflammatory response in a mammal, wherein said method comprises orally administering a composition comprising an anti-inflammatory amount of isolated live *Prevotella histicola* to said mammal, wherein said anti-inflammatory response is stimulated within said mammal.

2. The method of claim 1, wherein said mammal is a human.

3. The method of claim 1, wherein said anti-inflammatory response comprises increased expression of IL-10 compared to sham treated control mammals.

4. The method of claim 1, wherein said anti-inflammatory response comprises reduced expression of IL-17 compared to sham treated control mammals.

5. The method of claim 1, wherein said composition is a pill, tablet, or capsule.

6. The method of claim 1, wherein said composition is a pill, tablet, or capsule configured to deliver said *Prevotella histicola* to the intestines of said mammal.

7. The method of claim 1, wherein said *Prevotella histicola* are deposited as NRRL accession number B-50329.

* * * * *

SEQUENCE LISTING

```
<160> NUMBER OF SEQ ID NOS: 3

<210> SEQ ID NO 1
<211> LENGTH: 465
<212> TYPE: DNA
<213> ORGANISM: Prevotella histicola
<220> FEATURE:
<221> NAME/KEY: misc_feature
<222> LOCATION: 421
<223> OTHER INFORMATION: n = adenine, thymine, cytosine, or guanine

<400> SEQUENCE: 1
ggcttacaca tgcaagtcga ggggaaacgg cattaagtgc ttgcactttt tggacgtcga      60
ccggcgcacg ggtgagtaac gcgtatccaa ccttcccatg actaagggat aacctgccga     120
aaggcagact aatacctttat ggtcttcact gacggcatca gatgtgaagt aaagatttat    180
cggttatgga tggggatgcg tctgattagc ttgttggcgg ggtaacggcc caccaaggca     240
acgatcagta ggggttctga gaggaaggtc ccccacattg gaactgagac acggtccaaa     300
ctcctacggg aggcagcagt gaggaatatt ggtcaatggg cgagagcctg aaccagccaa     360
gtagcgtgca ggatgacggc cctatgggtt gtaaactgct tttgtatggg gataaagtca     420
ntcacgtgtg attgtttgca ggtaccatac gaataaggac cggct                     465

<210> SEQ ID NO 2
<211> LENGTH: 466
<212> TYPE: DNA
<213> ORGANISM: Prevotella histicola

<400> SEQUENCE: 2
ggcttaacac atgcaagtcg aggggaaacg gcattaagtg cttgcacttt ttggacgtcg      60
accggcgcac gggtgagtaa cgcgtatcca accttcccat gactaaggga taacctgccg     120
aaaggcagac taataccttta tggtcttcac tgacggcatc agatgtgaag taaagattta    180
tcggttatgg atggggatgc gtctgattag cttgttggcg gggtaacggc ccaccaaggc     240
aacgatcagt aggggttctg agaggaaggt cccccacatt ggaactgaga cacggtccaa     300
```

```
actcctacgg gaggcagcag tgaggaatat tggtcaatgg gcgagagcct gaaccagcca      360
agtagcgtgc aggatgacgg ccctatgggt tgtaaactgc ttttgtatgg ggataaagtc      420
agtcacgtgt gattgtttgc aggtaccata cgaataagga ccggct                    466
```

<210> SEQ ID NO 3
<211> LENGTH: 20
<212> TYPE: PRT
<213> ORGANISM: Artificial Sequence
<220> FEATURE:
<223> OTHER INFORMATION: synthetically generated peptide

<400> SEQUENCE: 3

```
Tyr Thr Thr Gly Ala Val Arg Gln Ile Phe Gly Asp Tyr Lys Thr Thr
1               5                   10                  15

Ile Cys Gly Lys
            20
```